United States Patent [19]

Burdea et al.

[11] Patent Number: 5,113,424
[45] Date of Patent: May 12, 1992

[54] APPARATUS FOR TAKING RADIOGRAPHS USED IN PERFORMING DENTAL SUBTRACTION RADIOGRAPHY WITH A SENSORIZED DENTAL MOUTHPIECE AND A ROBOTIC SYSTEM

[75] Inventors: Grigore C. Burdea, Highland Park; Stanley M. Dunn, Belle Mead; Paul J. Desjardins, Maplewood, all of N.J.

[73] Assignees: University of Medicine & Dentistry of New Jersey, Newark; Rutgers University, Piscataway, both of N.J.

[21] Appl. No.: 650,611

[22] Filed: Feb. 4, 1991

[51] Int. Cl.[5] .................................................. A61B 6/14
[52] U.S. Cl. .................................... 378/170; 378/168; 378/205; 378/197; 128/654; 128/653.1
[58] Field of Search ................. 378/170, 197, 98, 198, 378/205, 167, 168; 128/653 R, 654

[56] References Cited

U.S. PATENT DOCUMENTS

| | | | |
|---|---|---|---|
| 3,822,694 | 7/1974 | Mills | 128/653 R |
| 4,197,855 | 4/1980 | Lewin | 128/653 R |
| 4,223,228 | 9/1980 | Kaplan | 378/205 |
| 4,831,645 | 5/1989 | Guenther et al. | 378/205 |
| 4,949,370 | 8/1990 | Tanaka | 378/205 |

Primary Examiner—Janice A. Howell
Assistant Examiner—Kim-Kwok Chu
Attorney, Agent, or Firm—Klauber & Jackson

[57] ABSTRACT

Apparatus for taking dental x-rays used in performing subtraction radiography, includes an appliance for holding a dental x-ray film at a fixed position with respect to the teeth of a person, the appliance including a dental mold for holding the appliance in a fixed position on the teeth of the person, and a connecting member for holding the x-ray film in a fixed position relative to the teeth of the person and being mounted to the mold such that the x-ray film is positioned in the mouth at a set position; a magnetic source mounted at a fixed position in a room for producing a time-varying low frequency magnetic field; a magnetic sensor for sensing the magnetic field and for producing an output signal in response thereto, the magnetic sensor being mounted to the connecting member so as to be fixed in position relative to the x-ray film; an x-ray source for exposing the x-ray film; a robot manipulator having at least five degrees of freedom for moving the x-ray source in relation to the x-ray film, and having a free end with the x-ray source being fixed thereto; and a computer control for controlling the robot manipulator in response to the output signal from the sensor and in accordance with inverse kinematics so that the x-ray source is fixed in position with respect to the x-ray film, regardless of movement of the x-ray film.

19 Claims, 5 Drawing Sheets

APPARATUS FOR TAKING RADIOGRAPHS USED IN PERFORMING DENTAL SUBTRACTION RADIOGRAPHY WITH A SENSORIZED DENTAL MOUTHPIECE AND A ROBOTIC SYSTEM

BACKGROUND OF THE INVENTION

The present invention is directed to subtraction radiography, and more particularly, is directed to apparatus for taking radiographs used in performing dental subtraction radiography in real time, with a sensorized dental mouthpiece and a robotic system.

Radiographs are one of the most widely used diagnostic tools in dentistry. This remains true in spite of the inherent limitation that they provide only a two-dimensional projection or view of the area of interest.

However, as dental health has improved, the emphasis has shifted toward early detection of disease, requiring more exacting instruments. Nowhere is this more evident than in the diagnosis and treatment of periodontal disease. The goal is to be able to detect, as early as possible, small changes in the bony structure supporting the tooth. Studies have shown that disease can be detected earlier and with greater accuracy by looking at the difference between radiographs (x-ray films) taken over time, instead of a single radiograph. This "subtraction" technique can be accomplished optically by aligning films and viewing the same, or digitally, by digitizing each film and then subtracting corresponding picture elements to compute a difference image.

Digital subtraction radiography is one example of an imaging application which requires a measurement of change over time. Two images, each of which records the state of the dentition (teeth), are taken at different times. Since the normal anatomical structure should not change between the two films, the observed differences are indicative of growth or decay in the bony structure. The early studies used subtraction to detect lesions in between teeth and in the supporting structure of the teeth. See L. Ortman et al., "Subtraction radiography and Computer Assisted Densitometric Analyses of Standardized Radiographs" *Journal of Periodontal Research*, Vol. 20, pages 644-651, 1985; and M. Rethman et al., "Diagnosis of Bone Lesions by Subtraction Radiography", *Journal of Periodontal Research*, Vol. 56, pages 324-329, 1985. More recent papers cite applications of digital subtraction to measure bone loss (change in density) in the supporting structure of the teeth. See U. Braegger, "Digital Imaging in Periodontal Radiography", *Journal of Clinical Periodontoloov*, Vol. 15, pages 551-557, 1988; U. Braegger et al., "Color Conversion of Alveolar Bone Density Changes in Digital Subtraction Images", *Journal of Clinical Periodontoloogy*, Vol. 16, pages 209-214, 1989; U. Braegger et.al., "Remodeling of interdental alveolar bone after periodontal flap procedures assessed by means of computer assisted densitometric image analysis (CADIA)", *Journal of Clinical Periodontology*, Vol. 15, pages 558-564, 1988; and U. Braegger et.al., "Computer-Assisted Densitometric Image Analysis for the Assessment of Alveolar Bone Density Changes in Furcations", *Journal of Clinical Periodontoloov*, Vol. 16, pages 42-52, 1989.

However, these techniques present a unique imaging problem. The two radiographs must enclose the same field of view of the mouth and must be taken with the same geometry. In other words, the radiographs taken at different times must be in exact alignment, or stated otherwise, the x-ray films must be positioned at the identical location in the mouth and the x-ray gun and film must be aligned at the identical position and orientation for the different radiographs taken at different times.

The purpose of this subtraction is to eliminate the anatomic features not of interest, that is, the so-called "structured noise" in the image. However, if the radiographs are not in alignment, then the radiographs cannot be subtracted meaningfully. Specifically, if the imaging geometry is not the same, then the visual appearance of the structured noise is different and the difference will not be zero, yielding a false positive difference.

Thus, in all cases discussed above, the articles point out the difficulty in making the initial measurements, the difficulty in reproducing the original imaging geometry, and why this limits the use of digital subtraction radiography. The goal must therefore be to produce standardized views of the area of interest.

Much work to date has been done, using mechanical devices to fix the patient and the x-ray source at fixed positions. The proposed approach is based on accurately positioning the x-ray source; and then recognizing three-dimensional properties of the patient that are invariant in any view of the patient.

Thus, for example, the requirements of fixing the geometry to produce standardized radiographs have been recognized, by using a template to fix the mouth in position. See R. Webber et.al., "X-ray Image Subtraction as a Basis for Assessment of Periodontal Changes", *Journal of Periodontal Research*, Vol. 17, pages 509-511, 1982. Mechanical devices to standardize the imaging geometry have been used elsewhere. See, for example, H. Grondahl et.al., "Subtraction radiography for diagnosis of periodontal bone lesions", *Oral Suroerv*, Vol. 55, No. 2, pages 208-213, 1983; H. Grondahl et.al., "A digital subtraction technique for dental radiography", *Oral Surqerv*, Vol. 55, No. 1, pages 96-102, 1983; P. Janssen et.al., "The Detection of In Vitro Produced Periodontal Bone Lesions by Conventional Radiography and Photographic Subtraction Radiography Using Observers and Quantitative Digital Subtraction Radiography", *Journal of Clinical Periodontoloqv*, Vol. 16, pages 335-341, 1989; P. Janssen et.al., "The Effect of In-Vivo-Occurring Errors in the Reproducibility of Radiographs on the Use of the Subtraction Technique", *Journal of Clinical Periodontoloov*, Vol. 16, pages 53-58, 1989; and K. McHenry et.al., "Methodological Aspects and Quantitative Adjuncts to Computerized Subtraction Radiography", *Journal of Periodontal Research*, Vol. 22, pages 125-132, 1987. The articles all used subtraction in trials to quantitate bone loss. In the aforementioned article "The Effect of In-Vivo-Occurring Errors in the Reproducibility of Radiographs on the Use of the Subtraction Technique", Janssen et.al. found that the digital subtraction system was the most sensitive to measure subtle changes when compared to using a single radiograph or photographic subtraction, but required standardized geometry.

In the aforementioned article by Webber et.al., the authors noted that there were four sources of error leading to improper registration of a pair of radiographs, namely tissue changes, film, x-ray energy and inexact replication of imaging geometry. The first cannot be controlled other than by assumptions on the localization of the changes. The second can be controlled by the film type and processing chemicals. As to the third, Webber later studied the effects of polychromatic x-ray energy and showed that the effects of energy can be controlled. See R. Webber et.al., "The Effects of Beam Hardening on Digital Subtraction Radiography", *Journal of Periodontal Research*, Vol. 24, pages 53–58, 1989. The remaining problem therefore is that of controlling the imaging geometry.

To date, most approaches to this problem have relied on a model of radiograph formation of a point projection of x-rays along straight lines through the tissue. The x-rays are attenuated along these diverging straight line paths and form a distorted image on the film behind the hard tissue. As the source and/or film move with respect to the tissue, the appearance of the tissue on the film is changed non-linearly. Thus, to generate radiographs with the same appearance, it is important to reproduce the original imaging geometry. Following this line of reasoning, many studies of the subtraction technique have been reported that use mechanical fixtures to control the imaging geometry, that is, the position of the point source and the attenuation paths through the tissue. See, for example, K. Grondahl, "Influence of Variations in Projection Geometry on the Detectability of Periodontal Bone Lesions", *Journal of Clinical Periodontology*, Vol. 11, pages 411–420, 1984; the aforementioned second Janssen article at pages 53–58; M. Jeffcoat et.al., "A New Method for the Comparison of Bone Loss Measurements on Non-Standardized Radiographs", *Journal of Periodontal Research*, Vol. 19, pages 434–440, 1984; the aforementioned K. McHenry et.al. article; and the aforementioned Webber et.al. article at pages 509–511. Other studies have used compensatory algorithms to control the imaging geometry. See, for example, the aforementioned Jeffcoat et.al. article and P. van der Stelt, "Determination of Projections for Subtraction Radiography Based on Image Similarity Measurements", *Dento Maxillo Facial Radioloov*, Vol. 18, pages 113–117, 1989.

Thus, for example, a good example of a mechanical standardization system for subtraction radiography is given in the aforementioned Jeffcoat et.al. article. As explained therein, the x-ray source, patient and film are connected using an occlusal stent (bite block between the teeth) and cephalostat (fixture for the patient's head). The mechanical connection of the source, patient and film should restrict any variations to be in plane translations and rotations. By matching three anatomical features in the two films, the translations and rotations can be eliminated. The difficulty with these systems is two-fold. First, the use of a mechanical fixture or fixed imaging geometry provides that the field of view is restricted. In subtraction radiography, this means that only a limited portion of the dentition can be imaged. Secondly, disease processes are three dimensional, and not two-dimensional.

Various patents are known which disclose systems that are relevant to the present invention.

U.S. Pat. No. 4,223,228 to Kaplan discloses a dental x-ray aligning system having a permanent magnet mounted on the dental appliance or mouthpiece so that the magnet is in a fixed relation with respect to the x-ray film plate. The system also includes a sensor, in the form of Hall effect devices or probes, on the x-ray source in order to align the film and the source, as well as an indicator circuit. Basically, the indicator circuit, in response to the Hall effect probes, indicates the direction in which the apparatus should be moved in order to obtain alignment, as well as the distance between the apparatus and film plate.

However, the orientations permitted by this system are only translational orientations, and not rotational orientations. As a result, a truly accurate control cannot be achieved. Specifically, by using only a permanent magnet, only static alignment can be achieved source is performed manually, requiring human reading of a display screen. There is no inference of automatic orientations of the x-ray source and film without human intervention.

Still further, this system could not be utilized to detect the identical x-ray position at a subsequent time. This is because the receptacle for the x-ray film is clenched between the teeth of the user. Therefore, subsequent measurements may result in the patient holding the receptacle at a slightly different location, which would give a different reading. In other words, the permanent magnet is not fixed at a set position relative to the dentition, and therefore does not preserve the desired relationship with the teeth.

U.S. Pat. No. 4,197,855 to Lewin discloses a system for measuring the location, attitude and/or change in location of a body in space, and particularly, the position of the lower jaw or mandible with respect to the head. With this system, a permanent magnet which serves as a field generator is attached intraorally at any desired point of the lower jaw of the patient by means of an adhesive. An arrangement of several mutually perpendicular magnetic field sensors is mounted on the patient's cranium via a mounting so as to remain locationally fixed vis-a-vis the lower jaw and so as to provide a reference position as the latter is moved relative to the cranium.

Although this system can measure the position and orientation of the mandible with respect to sensors on the head, the system, as with Kaplan, uses a permanent magnet so as to suffer from the same problems. Also, this system is only applicable to the mandible, and not the maxillary arch. Specifically, this system is intended to be used for determining changes in cranio-facial attitude such as the amount by which the mandible opens with respect to the maxillary arch. There is no disclosure of extending this system for use with a radiologic system. Furthermore, this system is a measurement system, and does not provide any control of movement of any device, such an x-ray source, in response to the measurements.

U.S. Pat. No. 3,822,694 to Mills describes a similar system for measurement of jaw opening and orientation. Again, the measurements are made with respect to the cranium by the use of a mechanical attachment to a pair of sunglasses. The system is therefore provided only for measurement, and not for controlling any device, such as movement of an x-ray source. Furthermore, a permanent magnet is attached to the patient's gum using wax so that repeated measurements cannot be made. In sum, this system is only intended to measure gross cranio-facial motion parameters, and not to preserve sensor-tooth geometry.

U.S. Pat. No. 4,295,050 to Linden discloses a mechanical radiograph alignment system for positioning an x-ray camera in dental x-ray photography. Specifically, a bite block is connected to an arm perpendicular to the block, and a second guide is attached to the x-ray source that connects to the bite block to preserve the source-film orientation. However, this system uses a mechanical alignment which does not permit real time control, nor conservation of source-tooth geometry. Although the bite block and arm have marking symbols to make it possible to x-ray exactly the same area, the dental practitioner must make a note of the location of the bite block in relation to a suitable tooth by establishing which symbols are close to that tooth, which is not sufficiently exact during successive uses thereof. In other words, the system is entirely manual, and not automatic.

U.S. Pat. No. 1,719,106 to Cressler only discloses a system that assures repositioning of the x-ray film to tooth, by use of a mouth appliance. Specifically, a mass of material which becomes plastic when heated above normal body temperature but which is non-plastic and firm at or below the temperature of the body, is secured to the free end of the supporting wing of the main body that holds the x-ray film. In use, the patient bites down upon the mass and then the appliance is removed. The mass then cools so as to provide for accurate repositioning of the appliance in the patient's mouth at all times. The patent describes the device as having particular utility in stereoscopic work when it is essential that a plurality of views be taken of an object at different angles, or to take views illustrating the conditions in a particular tooth or a section of the jaw of a patient at different times, for comparison to determine the results of a course of treatment being pursued. However, this system is purely passive and does not have any means for controlling movement of an x-ray source.

U.S. Pat. No. 4,907,251 to Mork et al. discloses a patient positioning device in a medical panorama x-ray photographing apparatus. The system includes a position detecting sensor which detects the relative position of the dental arch of a patient to the x-ray photographing apparatus and a drive circuit for moving a tomograph forming assembly and/or a patient holding means in accordance with comparative data between the detected position data from the sensor relative to the position data of the tomographic zone to the x-ray photographing apparatus. However, there is no suggestion as to how to reposition an x-ray source with respect to dentition of interest. Furthermore, the installation is mechanical, and requires restraining the head of the patient.

U.S. Pat. No. 2,846,587 to Thurow discloses a cephalostat, commonly used in orthodontics. The patient is positioned and repositioned mechanically, by fixing the position of the bridge of the nose and the ears. Also, a standard x-ray source is used, and not one with automatic robotic control.

Other prior art of interest is found in U.S. Pat. Nos. 4,012,638 (Altschuler et.al.), 4,262,306 (Renner) and 4,887,286 (Seidenberg).

However, none of the above-discussed patents uses a magnetic sensor that permits static reposition in three dimensions. Furthermore, all of these installations are manual, and none provide for automatic control. Still further, none of the patents fixes the sensor-tooth-film geometry to a mouthpiece, nor fixes the x-ray source-tooth-film geometry. More importantly, none of the above-discussed patents can provide suitable resolution of the measurements needed to be made in today's dental environment.

OBJECTS AND SUMMARY OF THE INVENTION

Accordingly, it is an object of the present invention to provide apparatus for taking radiographs used in performing dental subtraction radiography, that overcomes the aforementioned problems with the prior art.

It is another object of the present invention to provide apparatus that operates in real time for taking radiographs used in performing dental subtraction radiography.

It is another object of the present invention to provide apparatus for taking radiographs used in performing dental subtraction radiography, that does not require fixing the patient in position in relation to the x-ray source.

It is still another object of the present invention to provide apparatus for taking radiographs used in performing dental subtraction radiography, that can detect small changes in the bony structure supporting the tooth at an early stage.

It is yet another object of the present invention to provide apparatus for taking radiographs used in performing dental subtraction radiography, in which the imaging geometry is reproduced exactly with simple control of existing radiograph systems.

It is a further object of the present invention to provide apparatus for taking radiographs used in performing dental subtraction radiography, in which the x-ray source can easily be repositioned by knowing the location of the patient and the desired imaging geometry.

It is a further object of the present invention to provide apparatus for taking radiographs used in performing dental subtraction radiography, that is not uncomfortable to the patient.

It is a further object of the present invention to provide apparatus for taking radiographs used in performing dental subtraction radiography, that allows all of the teeth of the patient to be x-rayed.

It is a further object of the present invention to provide apparatus for taking radiographs used in performing dental subtraction radiography, that is relatively easy and inexpensive to manufacture and use.

In accordance with an aspect of the present invention, apparatus for taking radiographs includes appliance means for holding a radiographic film at a fixed position with respect to a body part; magnetic source means for producing a magnetic field, the magnetic source means being mounted at a fixed position in a room; magnetic sensor means for sensing the magnetic field and for producing an output signal in response thereto, the magnetic sensor means being fixed in position relative to the appliance means; radiography means for exposing the radiographic film; robot means for moving the radiography means in relation to the radiographic film; and control means for controlling the robot means in response to the output signal from the magnetic sensor means so that the radiography means is in a fixed position with respect to the radiographic film, regardless of movement of the radiographic film.

In accordance with another aspect of the present invention, apparatus for taking dental radiographs includes appliance means for holding a radiographic film at a fixed position with respect to teeth of a person, the appliance means including dental mold means for holding the appliance means in a fixed position on the teeth of the person, and connecting means for holding the radiographic film in a fixed position relative to the teeth of the person, the connecting means being mounted to the dental mold means such that the radiographic film is positioned in the mouth of the person at a set position; magnetic source means for producing a time-varying low frequency magnetic field, the magnetic source means being mounted at a fixed position in a room; magnetic sensor means for sensing the magnetic field and for producing an output signal in response thereto, the magnetic sensor means being mounted to the connecting means so as to be fixed in position relative to the radiographic film; radiography means for exposing the radiographic film; robot means for moving the radiography means in relation to the radiographic film, the robot means including a robot manipulator capable of moving with at least five degrees of freedom, the robot manipulator having a free end, and the radiography means being fixed to the free end of the robot manipulator; and control means for controlling the robot means in response to the output signal from the magnetic sensor means so that the radiography means is in a fixed position with respect to the radiographic film, regardless of movement of the radiographic film.

In accordance with still another aspect of the present invention, apparatus for taking dental radiographs includes appliance means for holding a radiographic film at a fixed position with respect to teeth of a person, the appliance means including dental mold means for holding the appliance means in a fixed position on the teeth of the person, connecting means for holding the radiographic film in a fixed position relative to the teeth of the person, the connecting means being mounted to the dental mold means such that the radiographic film is positioned in the mouth of the person at a set position, and means for detachably connecting the sensor means to the connecting means; magnetic source means for producing a time-varying low frequency magnetic field, the magnetic source means being mounted at a fixed position in a room; magnetic sensor means for sensing the magnetic field and for producing an output signal in response thereto, the magnetic sensor means being mounted to the connecting means so as to be fixed in position relative to the radiographic film; radiography means for exposing the radiographic film; robot means for moving the radiography means in relation to the radiographic film, the robot means including a robot manipulator capable of moving with at least five degrees of freedom, the robot manipulator having a free end, and the radiography means being fixed to the free end of the robot manipulator; and computer control means for controlling the robot means in response to the output signal from the magnetic sensor means and in accordance with inverse kinematics so that the radiography means is in a fixed position with respect to the radiographic film, regardless of movement of the radiographic film.

DETAILED DESCRIPTION OF A PREFERRED EMBODIMENT

Digital subtraction radiography requires a system that provides good repeatability and accuracy for patient positioning, in order to correctly diagnose decay, movement or bone loss. As described previously, the aforementioned known dental subtraction radiography positioning systems are mechanical, uncomfortable for the patient and impractical for certain tooth positions, namely the teeth in the back of the mouth. As will now be described in greater detail, the present invention replaces the known mechanical systems with a sensorized system that does not use any direct mechanical link with the x-ray source, but rather, utilizes a robot arm as a positioning device that tracks a magnetic sensor attached to the patient's mouth.

Figure 1:
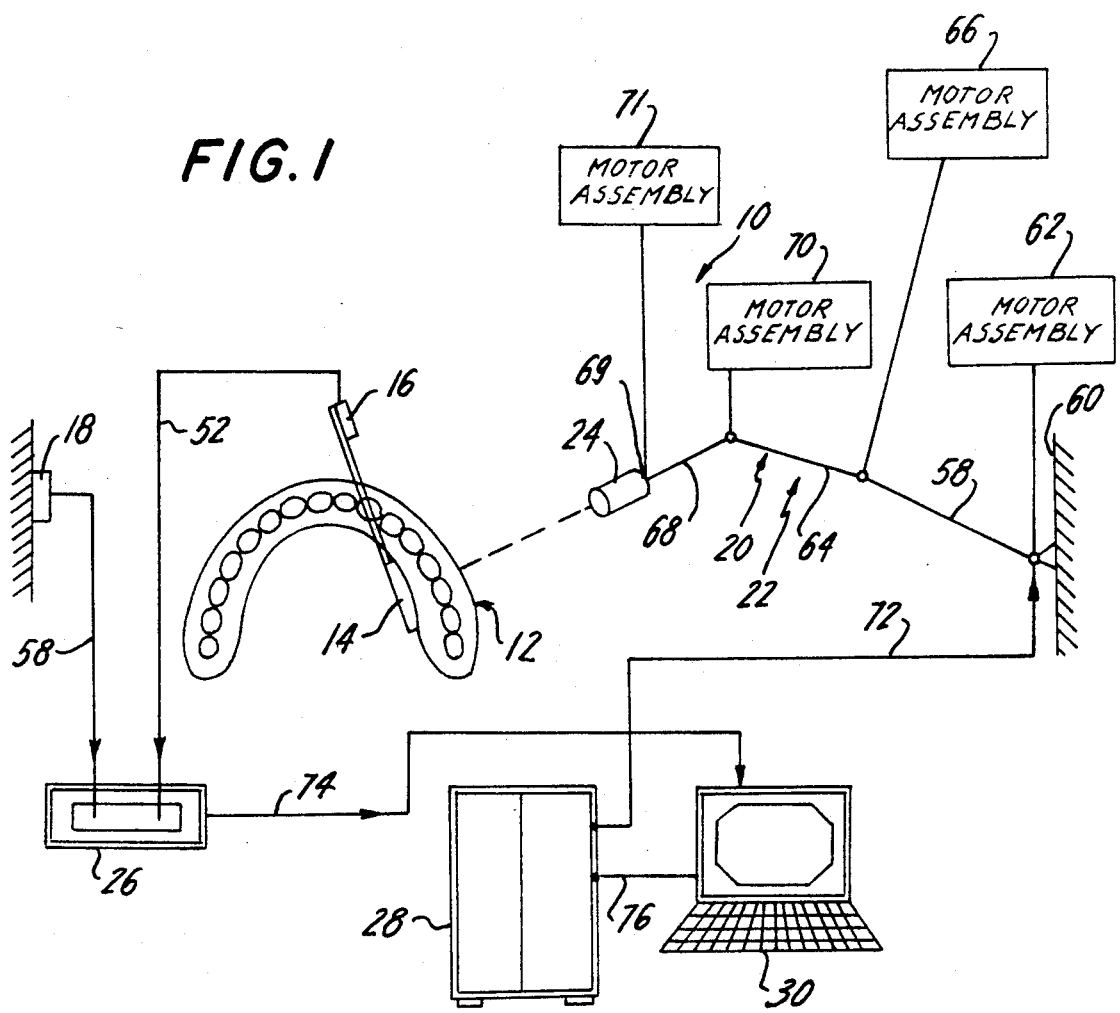
FIG. 1 is a schematic, block diagram of apparatus for taking radiograms used in performing dental subtraction radiography according to the present invention.

Referring now to the drawings in detail, and initially to FIG. 1 thereof, a schematic representation of apparatus 10 according to the present invention is shown to include a dental appliance or mouthpiece 12 having a radiographic film holder 14 and a detachable sensor 16 fixed thereto, a magnetic signal source 18, a robot manipulator 20 having an arm assembly 22 with an x-ray source 24 at the free end thereof, a sensor control unit 26, a robot control unit 28 and a host computer 30 used for programming, data transfer and analysis.

Figure 2:
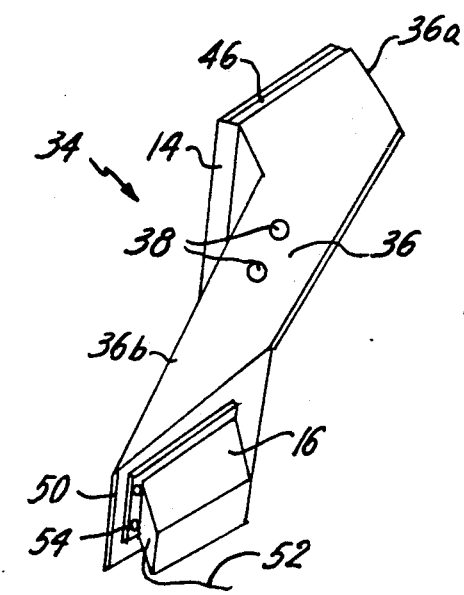
FIG. 2 is a perspective view of the connecting member of the dental appliance of FIG. 1.
Figure 3:
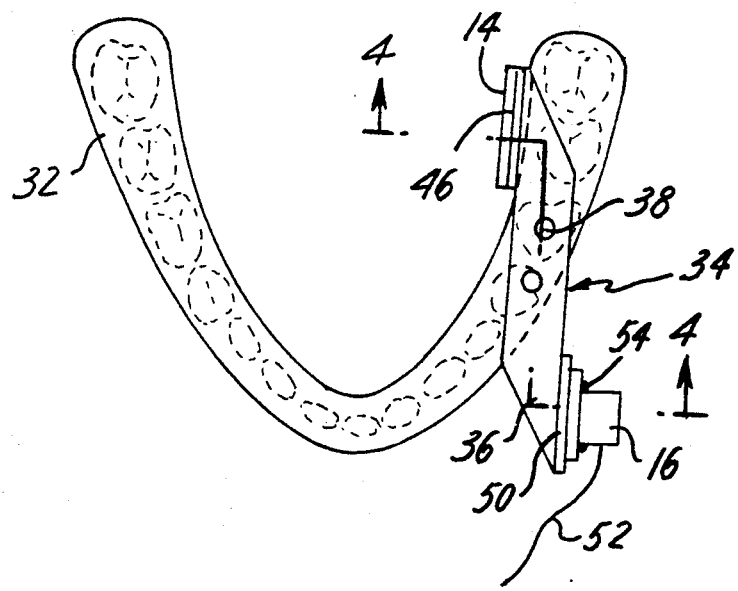
FIG. 3 is a top plan view of the dental appliance of Fig. 1.
Figure 4:
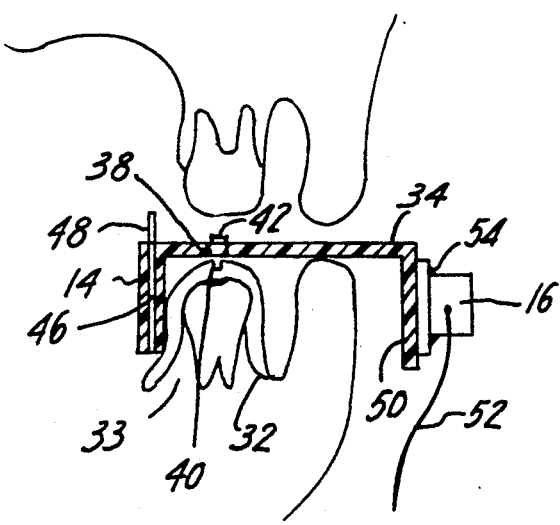
FIG. 4 is a cross-sectional view of the dental appliance of FIG. 3, taken along line 4—4 thereof.

As shown best in FIGS. 2-4, dental appliance 12 includes a dental mold 32 that is specially molded to an individual patient's teeth on the mandible 33, by standard dental molding procedures. As a result of the individualization of the dental mold, the dental mold is accurately and exactly positioned at the same location in the patient's mouth at all times.

Dental appliance 12 further includes a rigid plastic connecting member 34 which is connected to dental mold 32 in a fixed position relative thereto. Specifically, connecting member 34 includes a substantially L-shaped upper plate 36 with opposite ends 36a and 36b. Two holes 38 are provided in plate 36 between ends 36a and 36b thereof. Upper plate 36 is adapted to sit on the upper surface of dental mold 32 and be fixedly connected thereto. In this regard, at the position where the x-ray film is to be located, two threaded holes 40 are provided in the upper surface of dental mold 32, and two screws 42 are positioned through holes 38 and threadedly engaged within threaded holes 40. Normally, the dental practitioner maintains connecting member 34 in connected relation to dental mold 32 so that the two need not be reattached for each visit of the patient, whereby an exact registration is maintained at all times between dental mold 32 and connecting member 34. Although only two screw holes 40 have been shown in dental mold 32, it will be appreciated that additional screw holes can be provided at a number of different positions along dental mold 32, so that the dental practitioner can select the different teeth with which connecting member 34 will be associated. Thus, the present invention allows the placement of an x-ray film at different locations in the mouth, which is a definite advantage over mechanical stents that permit subtraction radiography only of the anterior (frontal) teeth with the same device. Of course, for different positions in the mouth, there will be different shaped connecting members.

It will be appreciated that, with connecting member 34 fixed to dental mold 32, end 36a of upper plate 36 extends to the lingual side of the teeth within the this regard, film holder 14 extends vertically down from end 36a to a position immediately behind the teeth of the patient. Generally film holder 14 defines a pocket 46 for holding an x-ray or radiographic film 48 with a friction fit at the same location at all times. In this manner, the x-ray film 48 is positioned at the identical location at all times behind the same teeth of the patient.

Connecting member 34 further includes a downwardly extending arm 50 at end 36b thereof, which has sensor 16 fixed thereto by suitable screws 54. In this manner, the patient can close his mouth, with sensor 16 being positioned outside of the mouth, along with the sensor wires 52 therefor. Further, with this arrangement, sensor 16 can be used repeatedly with different patients, with the only consumable elements being dental mold 32 and connecting member 34.

Sensor 16 is adapted to detect a time-varying low frequency magnetic field generated by magnetic signal source 18 (which is mounted at a fixed location in the room, such as the back of the dental chair), which information is used to determine its position and orientation in relation to magnetic signal source 18. Sensor 16 thereby performs constant monitoring of the position and orientation of the patient in three-dimensional space. Such monitoring is generally between 30 and 60 Hz. The sensor measurements are not affected by x-rays. Further, tests were performed, and it was determined that the sensor readings are not affected by the presence of metal in the mouth of the patient.

It will be appreciated that, by utilizing a time-varying low frequency magnetic field, rather than a fixed magnetic field which is generated by a permanent magnet, real time analysis can be utilized with respect to motion of the patient, that is, the necessary motion parameters can be detected. This is particularly important since the patient is constantly moving, even by small increments. Sensor 16 can be a Polhemus type sensor, for example, sold by McDonnell Douglas Electronics Co. of Colchester, VT.

Sensor 16 is connected by sensor wires 52 to sensor control unit 26 which samples the data from sensor 16. Sensor control unit 26 is also connected via wires 58 to magnetic signal source 18. Accordingly, since the fixed location of magnetic signal source 18 is known from previous measurements, and the location of sensor 16 relative to magnetic signal source 18 is also known, the location of sensor 16 in three-dimensional space can be determined. Further, since there is a fixed relation between sensor 16 and x-ray film 48 due to the rigid nature of connecting member 34, the location in three-dimensional space of x-ray film 48 can be determined by host computer 30 in response to the signals supplied by sensor control unit 26. Sensor control unit 26 is conventional, and is also sold, for example, by McDonnell Douglas Electronics Co. of Colchester, Vermont.

The present invention uses this x-ray film position data to control movement of x-ray source 24 so that the x-ray beam therefrom is always centered and perpendicular to x-ray film 48, with sensor 16 out of the imaging field, that is, out of the way of this path. In this regard, x-ray source 24 is mounted to the end of robot manipulator 20 which so moves x-ray source 24 to track sensor 16 attached to the patient's mouth. The weight of a conventional x-ray source 24 is approximately 20 kg, which is within the payload capability of several existing robot manipulators 20.

Figure 6:
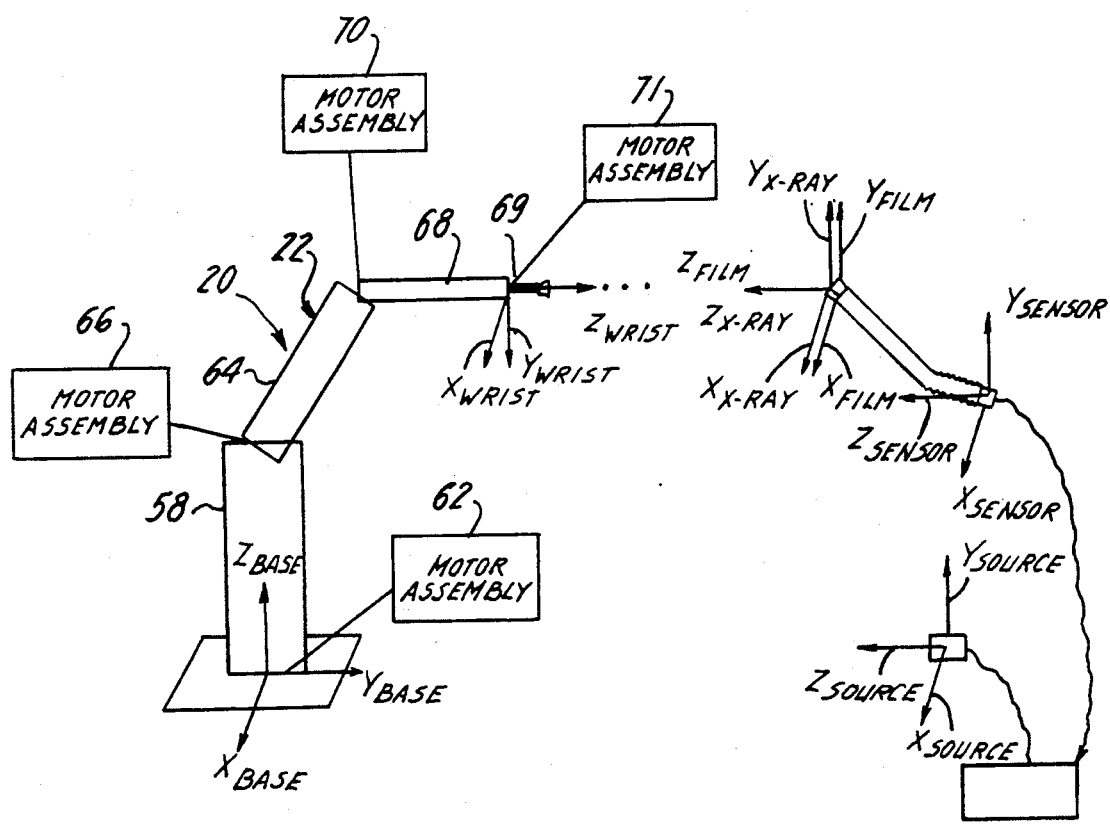
FIG. 6 is schematic diagram of the robot manipulator coordinate system in relation to the coordinate systems of the film, x-ray, sensor and magnetic source.

A typical robot manipulator 20 with which the present invention can be used, is schematically shown in FIGS. 1 and 6. For purposes of explanation, the description thereof will be simplified within the context of the present invention, it being clear that the actual operation of a robot manipulator will not operate with such discrete and independent movements as described herein.

As shown, arm assembly 22 of robot manipulator 20 includes a first movable link 58 connected to a base 60 which has a fixed spacial position. Link 58 is controlled by a motor assembly 62 to move with one degree of freedom. A second movable link 64 is connected to the free end of link 58 and is controlled by a second motor assembly 66 to move with one degree of freedom. Finally, a third movable link 68 is connected to the free end of link 64 and is controlled by a third motor assembly 70 to move with one degree of freedom. The movements of links 58, 64 and 68 determine the x, y and z position of the x-ray source. X-ray source 24 is connected at the free end of link 68 via a robot wrist 69 which is adapted to move in three different angular directions $\omega$, $\theta$ and $\phi$ corresponding to roll, pitch and yaw, by means of a motor assembly 71. It is noted that the symmetry of the x-ray beam can be exploited by aligning the rotation axis (roll) of wrist 69 with the longitudinal axis of x-ray source 24. Thus, the rotation angle $\Psi$ of wrist 69 becomes irrelevant, and a robot with only five degrees of freedom will suffice for use with the present application, thereby reducing the cost of the system.

Robot manipulator 20, and particularly the motor assemblies 62, 66, 70 and 71, are controlled by robot control unit 28, which is connected via wires 72, to robot manipulator 20. Sensor control unit 26 is connected via wires 74 (RS232 serial line) to host computer 30, which in turn, is interfaced via wires 76 to robot control unit 28, in order to control operation of robot manipulator 20 and to activate x-ray source 24.

In dental radiography applications, the position of robot wrist 69 with attached x-ray source 24, has to change as a function of the patient's position and orientation. Thus, if sensor 16 can provide the position and orientation of the targeted tooth, the robot can orient itself to follow sensor 16 and the tooth. The present invention thereby provides that sensor 16 is a six degree of freedom sensor, which provides position and orientation data (X, Y, Z, roll, pitch and yaw) that is needed to position the robot. Further, a high sensor bandwidth allows for small motions of the patient's head to be compensated for by the robot in real time.

In order to perform real time tooth tracking, the amount of computation performed by robot control unit 28 needs to be reduced. One way to reduce the amount of computation is to maintain a fixed geometrical relationship between the tooth and sensor 16, as in the present invention. Since dental mold 32 and connecting member 34 are rigid, the geometrical relationship between sensor 16 and the tooth is fixed, no matter how the patient turns his head. This relationship is computed off-line and stored in the memory of host computer 30, which can be a conventional PC computer. Host computer 30 downloads the relationship between sensor 16 and the tooth to robot control unit 28 along with its control signals that have been calculated therein, at the time of subsequent radiographs. While bone disease or decay may alter over time, the geometry of the mouth and the presence of dental appliance 12 assures a constant positioning of x-ray source 24 with respect to x-ray film 48. Of course, very large changes in the geometry of the mouth will require a new dental appliance 12, which will require repeating of the above process. Because of the exact relationship between radiographs taken at different times, the radiographs can be easily compared with known subtraction methods.

Figure 5:
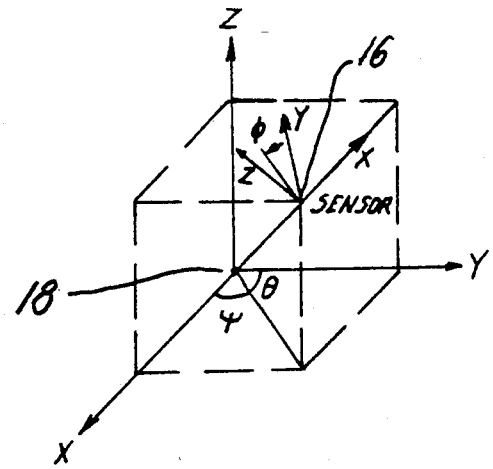
FIG. 5 is a diagram of the sensor and magnetic source coordinate systems.

In operation, sensor 16 transmits information containing six parameters. The first three parameters are x, y and z, representing the translation between sensor 16 and magnetic signal source 18. The second three parameters are $\Psi$, $\theta$ and $\phi$, where $\Psi$ is the rotation of the x and y coordinates about the z-axis, $\theta$ is the rotation of the z and the rotated x coordinates about the rotated y-axis, and $\phi$ is the rotation of the rotated y and z coordinates about the rotated x-axis, all as shown in FIG. 5. See, for example, Polhemus Navigation Sciences Division, "3-Space Isotrak User's Manual", McDonnell Douglas Electronics Co., Colchester, VT, 1987. With these six sensor parameters, a four by four transformation matrix $^{source}T_{sensor}$ expressing the position and orientation of sensor 16 with respect to source 18 is given as follows:

$$^{source}T_{sensor} = T_{Z,\Psi} T_{Y,\theta} T_{X'',\phi} T_{trans} \cdots \quad (1)$$

The use of Y' nd X'' represent the subsequent rotation of the axes, as described above.

Another transformation $^{sensor}T_{tooth}$ expresses the position of the targeted tooth with respect to sensor 16 on dental appliance 12. This transformation depends on the characteristics of the patient and connecting member 34, and therefore has to be determined for each patient, once dental appliance 12 is built. The transformation which gives the position of the tooth of interest in magnetic source coordinates is:

$$^{source}T_{tooth} = {}^{source}T_{sensor} {}^{sensor}T_{tooth} \cdots \quad (2)$$

While $^{sensor}T_{tooth}$ is fixed (but patient dependent), $^{source}T_{sensor}$ will vary as a function of head position and orientation. In this way, $^{source}T_{tooth}$ tracks the position of the patient's tooth, with respect to the fixed system of coordinates of the source.

Another transformation that is needed is $^{wrist}T_{x\text{-}ray}$ between the system of coordinates attached to x-ray source 24 and that attached to robot wrist 69. In order to take advantage of the axial symmetry, the origin $OX_{x\text{-}ray}Y_{x\text{-}ray}Z_{x\text{-}ray}$ of x-ray source 24 is chosen so that $Z_{x\text{-}ray}$ points towards, and is coaxial with wrist 69. The origin $OX_{x\text{-}ray}Y_{x\text{-}ray}Z_{x\text{-}ray}$ is located at a fixed distance L from robot wrist 69. Since it is desired to maintain a fixed distance between x-ray source 24 and the tooth, this distance L, in operation, will ideally correspond to the distance of x-ray source 24 to the patient. $^{wrist}T_{x\text{-}ray}$ is fixed and given by a matrix as follows:

$$^{wrist}T_{x\text{-}ray} = \begin{bmatrix} 1 & 0 & 0 & 0 \\ 0 & -1 & 0 & 0 \\ 0 & 0 & -1 & L \\ 0 & 0 & 0 & 1 \end{bmatrix} \quad (3)$$

In order to orient itself, the robot needs to know the patient position given in its own robot coordinates as $^{base}T_{tooth}$. If source 18 is placed at a fixed and known location with respect to robot base 60, then the transformation $^{base}T_{tooth}$ can also be determined. The position of the patient with respect to the robot is then given by:

$$^{base}T_{tooth} = {}^{base}T_{source} {}^{source}T_{tooth} \cdots \quad (4)$$

The relationship between the various origins and spacial systems of base 60, wrist 69, film 48, x-ray source 24, sensor 16 and source 18, is shown in FIG. 6.

Figure 7:
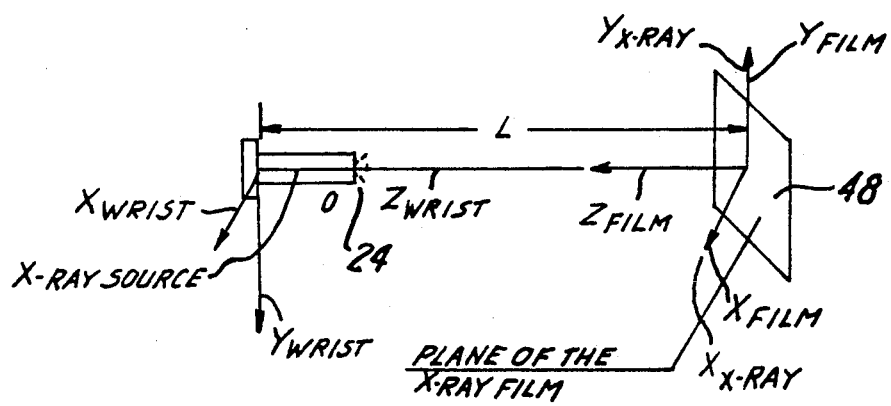
FIG. 7 is a diagram showing alignment of the x-ray source and the film, in the targeted film/tooth plane.

The alignment between x-ray source 24 and the targeted tooth is one of the keys to reproducibility of the images. In accordance with the present invention, x-ray source 24 is aligned perpendicular to the plane of x-ray film 48, so that the origin $OX_{x\text{-}ray}Y_{x\text{-}ray}Z_{x\text{-}ray}$ of x-ray source 24 and the roigin $OX_{film}Y_{film}Z_{film}$ of x-ray film 48 coincide. This is shown best in FIG. 7. Particularly, the alignment condition sufficient to obtain the robot arm position is:

$$^{base}T_{x\text{-}ray} = {}^{base}T_{tooth} \cdots \quad (5)$$

or $$^{base}T_{wrist} = {}^{base}T_{tooth} {}^{wrist}T_{x\text{-}ray}^{-1} \cdots \quad (6)$$

where $$^{wrist}T_{x\text{-}ray}^{-1} = {}^{wrist}T_{x\text{-}ray} = \begin{bmatrix} 1 & 0 & 0 & 0 \\ 0 & -1 & 0 & 0 \\ 0 & 0 & -1 & L \\ 0 & 0 & 0 & 1 \end{bmatrix} . \quad (7)$$

The reason that the matrices of equations (3) and (7) are the sme is because of the mirror imae symmetry of the chosen systems.

Equation (6) represents the solution which is fed into robot control unit 28 by computer 30. This, in turn, determines the robot joint positions based on inverse kinematics calculations. See, for example, K. Fu, *Robitcs: control, Sensing, Vision, and Intelligence,* McGraw-Hill Company, New York, NY 1987, for a discussion of inverse kinematics with respect to robotic control. In actuality, robotic systems that can be used with the present invention use inverse kinemtics based on precise dimensions measured by the manufacturers and kept secret by the manufacturers. The calculations for the inverse kinematics are then built into the robotic control by the manufactuerer, and need not be discussed herein.

It will be appreciated that the solution given by Equation (6) is a static solution. In order to limit the adverse effects of robot dynamics, it is necessary to have a high bandwidth in the control loop, and relatively small and slow patient head motions. In the present invention, the bandwidth of sensor 16 is the limiting factor.

Figure 8:
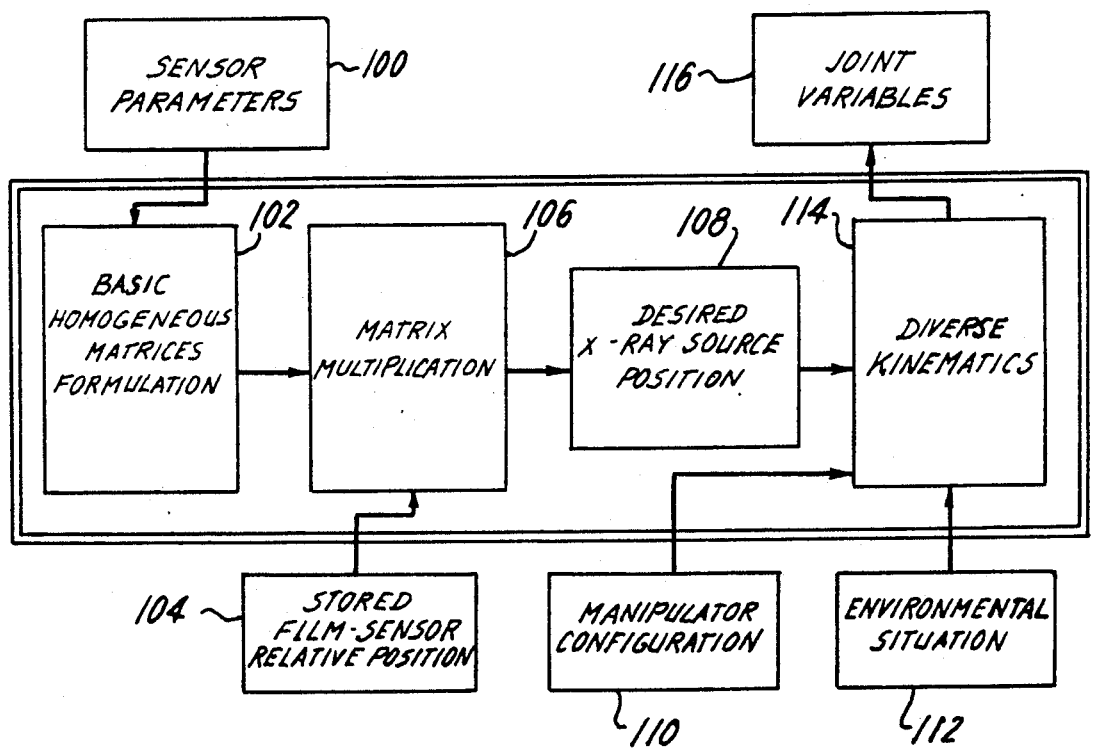
FIG. 8 is a flow chart showing operation of the present invention.

The basic flow chart of operation of the present invention is shown in FIG. 8.

Specifically, in step 100, the aforementioned six parameters from sensor 16 are read, and supplied to host computer 30. Thereafter, in step 102, host computer 30 applies the sensor parameters to the basic homogeneous matrices formulations described above, particularly with respect to equation (1). The fixed relative position of film 48 to sensor 16 is then read from memory by host computer, in step 104. From this relative position, and the results of step 102, the matrix multiplication of equations (2), (4) and (6) are performed by host computer 30, in step 106, to obtain the desired x-ray source position 108. Based on the configuration 110 of robot manipulator 20, the environmental situation 112 (such as the absence of an obstacle in the robot workspace), and the desired x-ray source position 108, the inverse kinematics is determined in step 114, whereby robot control unit 28 determines the joint variables 116 to control the various motor assemblies to move x-ray source 24 to the desired x-ray source position 108.

Accordingly, with the present invention, there is a sensorized dental appliance that allows accurate measurement of targeted tooth position without supplemental mechanical alignment, whereby the need for mechanical contact with the x-ray source is avoided. Therefore, the present system can be used to image posterior, as well as anterior, teeth. The present invention also provides for manipulation of an x-ray source by a robotic system in response to the sensitized dental appliance with great accuracy.

It will be appreciated that the present invention has applicability outside of the dental field, and can be used, for example, for non-dental subtraction radiography, such as with the lungs, heart and the like, and even for radiographs with desired viewing directions outside of the subtraction radiography field.

Having described a specific preferred embodiment of the invention with reference to the accompanying drawings, it will be appreciated that the present invention is not limited to that precise embodiment and that various changes and modifications can be effected therein by one of ordinary skill in the art, without departing from the scope or spirit of the invention as defined in the appended claims.

What is claimed is:

1. Apparatus for taking radiographs, comprising:
   appliance means for holding a radiographic film at a fixed position with respect to a body part;
   magnetic source means for producing a magnetic field, the magnetic source means being mounted at a fixed position in a room;
   magnetic sensor means for sensing said magnetic field and for producing an output signal in response thereto, said magnetic sensor means being fixed in position relative to said appliance means;
   radiography means for exposing the radiographic film;
   robot means for moving said radiography means in relation to the radiographic film; and
   control means for controlling said robot means in response to the output signal from said magnetic sensor means so that said radiography means is in a fixed position with respect to said radiographic film, regardless of movement of said radiographic film.

2. Apparatus according to claim 1, wherein said appliance means includes dental mold means for holding said appliance means in a fixed position on teeth of a person and connecting means for holding said radiographic film and said magnetic sensor means in said fixed position relative to each other, said connecting means being mounted to said dental mold means.

3. Apparatus according to claim 2, wherein said connecting means is mounted to said dental mold such that said radiographic film is positioned in the mouth of the person at a set position, and said sensor means is positioned outside of the mouth of the person.

4. Apparatus according to claim 2, further including means for detachably connecting said sensor means to said connecting means.

5. Apparatus according to claim 1, wherein said magnetic source means includes means for producing a time-varying low frequency magnetic field.

6. Apparatus according to claim 1, wherein said radiography means includes an x-ray source.

7. Apparatus according to claim 1, wherein said robot means includes a robot manipulator capable of moving with at least five degrees of freedom, said robot manipulator having a free end, and said radiography means is fixed to the free end of said robot manipulator.

8. Apparatus according to claim 1, wherein said control means includes computer means for controlling said robot means in response to said output signal and in accordance with inverse kinematics.

9. Apparatus according to claim 8, wherein said control means further includes sensor control means for interfacing said sensor means to said computer means, and robot control means for interfacing said computer means to said robot means.

10. Apparatus for taking dental radiographs, comprising:
    (a) appliance means for holding a radiographic film said appliance means including:
        (i) dental mold means for holding said appliance means in a fixed position on the teeth of the person, and
        (ii) connecting means for holding said radiographic film in a fixed position relative to the teeth of the person, said connecting means being mounted to said dental mold means such that said radiographic film is positioned in the mouth of the person at a set position;
    (b) magnetic source means for producing a time-varying low frequency magnetic field, said magnetic source means being mounted at a fixed position in a room;
    (c) magnetic sensor means for sensing said magnetic field and for producing an output signal in response thereto, said magnetic sensor means being mounted to said connecting means so as to be fixed in position relative to said radiographic film;
    (d) radiography means for exposing said radiographic film;
    (e) robot means for moving said radiography means in relation to said radiographic film, said robot means including a robot manipulator capable of moving with at least five degrees of freedom, said robot manipulator having a free end, and said radiography means being fixed to the free end of said robot manipulator; and
    (f) control means for controlling said robot means in response to said output signal from said magnetic sensor means so that said radiography means is in a fixed position with respect to said radiographic film, regardless of movement of said radiographic film.

11. Apparatus according to claim 10, further including means for detachably connecting said sensor means to said connecting means.

12. Apparatus according to claim 10, wherein said magnetic source means includes means for producing a time-varying low frequency magnetic field.

13. Apparatus according to claim 10, wherein said radiography means includes an x-ray source.

14. Apparatus according to claim 10, wherein said control means includes computer means for controlling said robot means in response to said output signal and in accordance with inverse kinematics.

15. Apparatus according to claim 14, wherein said control means further includes sensor control means for interfacing said sensor means to said computer means, and robot control means for interfacing said computer means to said robot means.

16. Apparatus for taking dental radiographs, comprising:
(a) appliance means for holding a radiographic film at a fixed position with respect to teeth of a person, said appliance means including:
   (i) dental mold means for holding said appliance means in a fixed position on the teeth of the person,
   (ii) connecting means for holding said radiographic film in a fixed position relative to the teeth of the person, said connecting means being mounted to said dental mold means such that said radiographic film is positioned in the mouth of the person at a set position, and
   (iii) means for detachably connecting said sensor means to said connecting means;
(b) magnetic source means for producing a time-varying low frequency magnetic field, said magnetic source means being mounted at a fixed position in a room;
(c) magnetic sensor means for sensing said magnetic field and for producing an output signal in response thereto, said magnetic sensor means being mounted to said connecting means so as to be fixed in position relative to said radiographic film;
(d) radiography means for exposing said radiographic film;
(e) robot means for moving said radiography means in relation to said radiographic film, said robot means including a robot manipulator capable of moving with at least five degrees of freedom, said robot manipulator having a free end, and said radiography means being fixed to the free end of said robot manipulator; and
(f) computer control means for controlling said robot means in response to said output signal from said magnetic sensor means and in accordance with inverse kinematics so that said radiography means is in a fixed position with respect to said radiographic film, regardless of movement of said radiographic film.

17. Apparatus according to claim 16, wherein said radiography means includes an x-ray source.

18. Apparatus according to claim 16, wherein said control means includes computer means for controlling said robot means in response to said output signal and in accordance with inverse kinematics.

19. Apparatus according to claim 18, wherein said control means further includes sensor control means for interfacing said sensor means to said computer means, and robot control means for interfacing said computer means to said robot means.

* * * * *